United States Patent
Gupta et al.

(10) Patent No.: US 10,130,271 B1
(45) Date of Patent: Nov. 20, 2018

(54) SERIAL FUSION OF EULERIAN AND LAGRANGIAN APPROACHES FOR REAL-TIME HEART RATE ESTIMATION

(71) Applicant: Tata Consultancy Services Limited, Mumbai (IN)

(72) Inventors: Puneet Gupta, Kolkata (IN); Brojeshwar Bhowmick, Kolkata (IN); Arpan Pal, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 15/900,783

(22) Filed: Feb. 20, 2018

(30) Foreign Application Priority Data

Jul. 11, 2017 (IN) .............................. 201721024390

(51) Int. Cl.
- *A61B 5/024* (2006.01)
- *A61B 5/00* (2006.01)
- *G06K 9/00* (2006.01)

(52) U.S. Cl.
CPC ...... *A61B 5/02405* (2013.01); *A61B 5/02416* (2013.01); *A61B 5/7246* (2013.01);
(Continued)

(58) Field of Classification Search
CPC ........... G06T 19/00; G06T 2207/30201; G06T 2207/30088; G06T 2207/30104;
(Continued)

(56) References Cited

U.S. PATENT DOCUMENTS 7,167,816 B1    1/2007  Olovsson
2011/0251493 A1 10/2011 Poh et al.
(Continued)

OTHER PUBLICATIONS

Wu, H-Y. et al. (Jul. 2012). "Eulerian Video Magnification for Revealing Subtle Changes in the World," *Journal ACM Transactions on Graphics* (*TOG*), vol. 31, issue 4; 8 pages.
(Continued)

*Primary Examiner* — Edward Park
(74) *Attorney, Agent, or Firm* — Finnegan, Henderson, Farabow, Garrett & Dunner LLP (57) ABSTRACT

Traditional electrocardiography (ECG) and photo-plethysmography (PPG) based HR estimation require human skin contact which is not only user uncomfortable, but also infeasible when multiple user monitoring is required or extreme sensitive conditions is a prime concern as in the case of monitoring neonates, sleeping human and skin damaged patients. Temporal signals depicting the motion or color variations in the frames across time, are estimated from a Region of Interest using Eulerian or Lagrangian approaches. However, the Eulerian approach fails under improper illumination, inappropriate camera focus or human factors like skin color. Likewise, Lagrangian approach is highly time-consuming and may fail when few or less discriminatory features are available for tracking. The present disclosure provides a poorness measure that is indicative of when an approach fails and facilitates serial fusion of the two approaches. Switching to an appropriate approach results in accurate heart rate estimation.

13 Claims, 7 Drawing Sheets

(52) U.S. Cl.
CPC .......... *A61B 5/7282* (2013.01); *G06K 9/0051* (2013.01); *G06K 2009/00939* (2013.01)

(58) Field of Classification Search
CPC ................ G06T 7/0012; A61B 5/0077; G06K 2009/00939; G06K 9/00302
See application file for complete search history.

(56) References Cited

U.S. PATENT DOCUMENTS

| | | |
|---|---|---|
| 2013/0077823 A1 | 3/2013 | Mestha et al. |
| 2013/0345568 A1 | 12/2013 | Mestha et al. |
| 2015/0242545 A1 | 8/2015 | Cho et al. |
| 2015/0264567 A1* | 9/2015 | Sensharma ........... H04W 12/06 455/411 |
| 2018/0064335 A1* | 3/2018 | Rutschman .............. A61B 3/12 |

OTHER PUBLICATIONS

Chambino, P.B. (2013). Android-based implementation of Eulerian Video Magnification for vital signs monitoring (Oral Examination). Retrieved from https://repositorio-aberto.up.pt/bitstream/10216/68234/2/26316.pdf.

* cited by examiner

SERIAL FUSION OF EULERIAN AND LAGRANGIAN APPROACHES FOR REAL-TIME HEART RATE ESTIMATION

PRIORITY CLAIM

This U.S. patent application claims priority under 35 U.S.C. § 119 to: Indian Patent Application No. 201721024390, filed on 11 Jul. 2017. The entire contents of the aforementioned application are incorporated herein by reference.

TECHNICAL FIELD

The embodiments herein generally relate to heart rate estimation through non-invasive measures, and more particularly to systems and methods for serial fusion of Eulerian and Lagrangian approaches for real-time heart rate estimation.

BACKGROUND

Camera-equipped devices are ubiquitous and proliferating day-to-day life. Accurate heart rate (HR) estimation from face videos acquired from low cost cameras in a non-contact manner can be used in many real-world scenarios and hence require rigorous exploration. HR estimation using face videos is based on the phenomenon that color and motion variations in the face videos are closely related to heart beat. The variations also contain noise due to facial expressions, respiration, eye blinking and environmental factors. Temporal signals depicting motion or color variations in frames across time are estimated from Region of Interest (ROI) using Eulerian or Lagrangian approaches. In a Lagrangian approach, temporal signals are determined by explicitly tracking the ROI or discriminating features over time. Such tracking is computationally expensive hence usually temporal signals are estimated using Eulerian approach, i.e., temporal signals are obtained by fixing the ROI and analyzing its variations. The Eulerian approach however works accurately for small variations.

SUMMARY

Embodiments of the present disclosure present technological improvements as solutions to one or more of the above-mentioned technical problems recognized by the inventors in conventional systems.

In an aspect, there is provided a processor implemented method comprising: dividing a face video of interest into intervals of pre-defined length; computing heart rate (HR) for each of the intervals based on temporal signals obtained by Eulerian approach; determining a first poorness measure based on heart rate variability in consecutive time intervals for temporal signals obtained by the Eulerian approach; computing heart rate based on Lagrangian approach, if the first poorness measure is greater than a pre-defined threshold; determining a second poorness measure based on heart rate variability in consecutive time intervals for temporal signals obtained by the Lagrangian approach; and identifying, in real-time, heart rate associated with lesser of the first poorness measure and the second poorness measure as the heart rate for a corresponding face in the face video.

In another aspect, there is provided a system comprising: one or more data storage devices operatively coupled to the one or more processors and configured to store instructions configured for execution by the one or more processors to: divide a face video of interest into intervals of pre-defined length; compute heart rate (HR) for each of the intervals based on temporal signals obtained by Eulerian approach; determine a first poorness measure based on heart rate variability in consecutive time intervals for temporal signals obtained by the Eulerian approach; compute heart rate based on Lagrangian approach, if the first poorness measure is greater than a pre-defined threshold; determine a second poorness measure based on heart rate variability in consecutive time intervals for temporal signals obtained by the Lagrangian approach; and identify, in real-time, heart rate associated with lesser of the first poorness measure and the second poorness measure as the heart rate for a corresponding face in the face video.

In yet another aspect, there is provided a computer program product comprising a non-transitory computer readable medium having a computer readable program embodied therein, wherein the computer readable program, when executed on a computing device, causes the computing device to: divide a face video of interest into intervals of pre-defined length; compute heart rate (HR) for each of the intervals based on temporal signals obtained by Eulerian approach; determine a first poorness measure based on heart rate variability in consecutive time intervals for temporal signals obtained by the Eulerian approach; compute heart rate based on Lagrangian approach, if the first poorness measure is greater than a pre-defined threshold; determine a second poorness measure based on heart rate variability in consecutive time intervals for temporal signals obtained by the Lagrangian approach; and identify, in real-time, heart rate associated with lesser of the first poorness measure and the second poorness measure as the heart rate for a corresponding face in the face video.

In an embodiment of the present disclosure, the pre-defined length is optimized such that peak due to noise is averted and HR variability is available.

In an embodiment of the present disclosure, the pre-defined length is 180 frames.

In an embodiment of the present disclosure, the one or more hardware processors are further configured to determine the first poorness measure and the second poorness measure by: normalizing the temporal signals in an interval; maximizing Kurtosis associated with the normalized temporal signal to extract photoplethysmogram (PPG) signal; transforming the PPG signal to frequency domain; computing the heart rate based on frequency corresponding to maximum amplitude associated with the PPG signal; and computing the first poorness measure or the second poorness measure as a function of the heart rate variability in consecutive time intervals and permissible variations in heart rate in beats per minute (bpm).

In an embodiment of the present disclosure, the pre-defined threshold is based on number of intervals.

In an embodiment of the present disclosure, the pre-defined threshold is one third of the number of intervals.

It is to be understood that both the foregoing general description and the following detailed description are exemplary and explanatory only and are not restrictive of the embodiments of the present disclosure, as claimed.

BRIEF DESCRIPTION OF THE DRAWINGS

The embodiments herein will be better understood from the following detailed description with reference to the drawings, in which.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Before setting forth the detailed explanation, it is noted that all of the discussion below, regardless of the particular implementation being described, is exemplary in nature, rather than limiting.

Accurate heart rate (HR) is essential to assess physiological, pathological and physiological parameters of the circulatory system, and subsequently analyzing several cardiac diseases, stress monitoring and emotion detection. Existing hemodynamics approaches, electrocardiography (ECG) and photoplethysmography (PPG) involve skin contact and thus these are user uncomfortable and restricted for single user monitoring. Moreover, they are insufficient to analyze sleeping humans, exercising humans, skin damaged humans and neonates. Known HR estimation systems based on face videos are based on either Eulerian or Lagrangian approaches. Temporal signals may be extracted using Lagrangian perspective where discriminating features are explicitly tracked over time. Better tracking may be performed by clustering similar trajectories, reconstructing noisy samples and selecting several informative ROI or features. Such tracking mechanisms are highly time-consuming and they may be spurious when few or less discriminatory features are available for tracking due to poor lighting conditions. These issues restrict applicability of Lagrangian temporal signals in near real-world scenarios. Alternatively, Eulerian perspective may be used where temporal signals may be obtained by fixing ROI at some locations and analyzing the variations therein. It avoids time consuming tracking of ROI. Implicitly, this approach relies on the principles of optical flow algorithms and works accurately but mostly for small variations. As an instance, ROI may be extracted from each frame and its mean values for each color channel may be used to represent three signals. Eulerian temporal signals may fail to provide accurate HR due to improper illumination, inappropriate camera focus or human factors (for example, skin color). The Applicant has addressed this challenge in Indian Application No. 201721009872 by providing a quality measure that may be used with the Eulerian approach for improved HR estimation.

The methods and systems of the present disclosure facilitate switching between the approaches by serial fusion such that their capabilities are best utilized. Firstly, the methods and systems of the present disclosure mitigate noise but still the Eulerian temporal signals may fail in some cases to provide accurate HR due to improper illumination, inappropriate camera focus or human factors (for example, skin color). Such cases are determined using a poorness measure and in these cases, both the Eulerian and Lagrangian temporal signals are employed for better HR estimation by serial fusion wherein switching to an appropriate approach is initiated based on a poorness measure.

Referring now to the drawings, and more particularly to FIGS. 1 through 7, where similar reference characters denote corresponding features consistently throughout the figures, there are shown preferred embodiments and these embodiments are described in the context of the following exemplary system and method.

Figure 1:
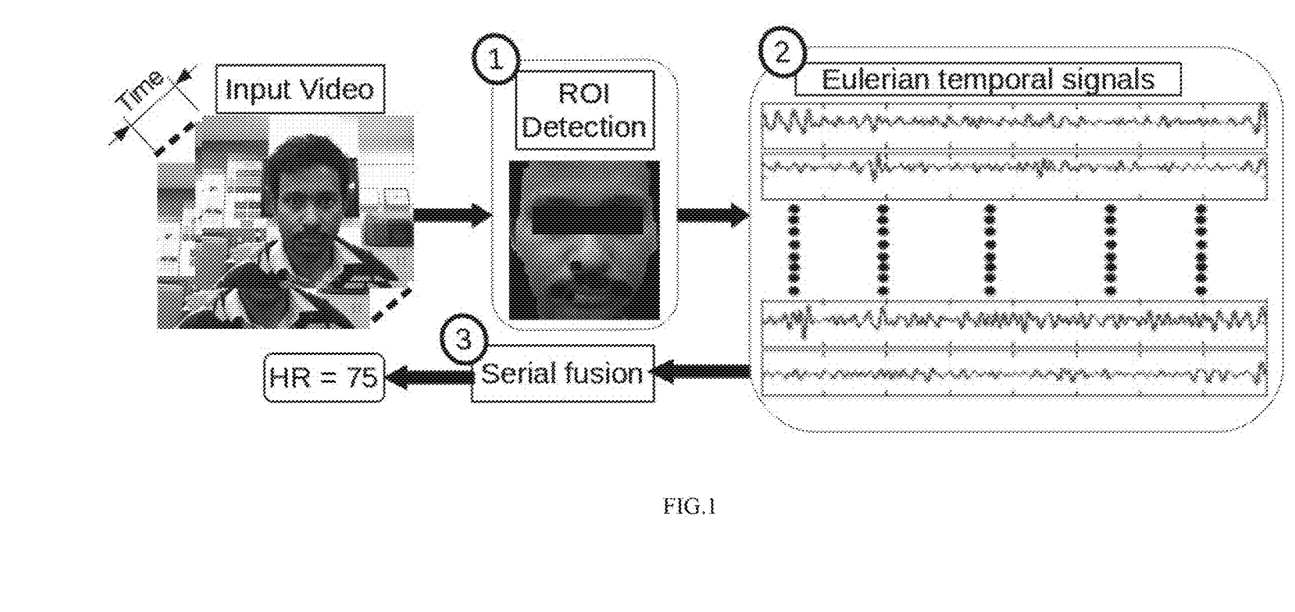
FIG. 1 illustrates an exemplary overall architecture of a system for serial fusion of Eulerian and Lagrangian approaches for real-time heart rate estimation, in accordance with an embodiment of the present disclosure.

FIG. 1 illustrates an exemplary overall architecture of a system for serial fusion of Eulerian and Lagrangian approaches for real-time heart rate estimation, in accordance with an embodiment of the present disclosure. As illustrated in FIG. 1, there are three stages viz., Region of Interest (ROI) detection, extraction of Eulerian temporal signals and serial fusion for estimating heart rate (HR). Initially, facial skin areas are detected and temporal signals are determined from the areas using Eulerian approach. Eventually, serial fusion is used to estimate HR which evaluates the effectiveness of the Eulerian temporal signals and decides whether to use Lagrangian temporal signals or not for better HR estimation.

ROI detection: In an embodiment, Viola-Jones face detector may be applied to a first frame of a face video to determine face regions. Non-face pixels and inevitable eye blinking in the face video can deteriorate HR estimation; hence they may be first determined using skin detection and Viola-Jones eyes detector respectively, and subsequently removed from facial areas. Face boundary pixels having light color or motion variations may also contribute to noise and introduce enormous variations in temporal signals. Thus, the boundary pixels may be removed in an embodiment using morphological erosion operation. Considering a complete face as one ROI may result in erroneous HR estimation because: i) different face regions exhibit different color variations depending on the placement of unevenly distributed face arteries; and ii) the facial emotion introduces noise in some face regions that can result in spurious HR estimation. Thus the remaining area is divided into several square blocks and each block is considered as ROI. The block-size may be chosen such that the remaining area contains about 10 blocks in the horizontal direction. For ease of explanation, HR estimation using a single face is discussed. Finally, all detected faces in the face video follow the same methodology as described hereinafter for HR estimation.

Extraction of Eulerian temporal signals: Green channel exhibits the strongest plethysmographic signals amongst all the color channels. Thus, the mean green value of the pixels in a block is used to define the temporal signal. Accordingly, if $S^i$ denotes the temporal signal for $i^{th}$ block and the input video consists of f frames, then, $$S^i = [s_1^i, s_2^i, \ldots, s_f^i] \to (1)$$

wherein $s_k^i$ is the mean green value of pixels of $i^{th}$ block in $k^{th}$ frame.
Thus if $B_k^i$ is the $i^{th}$ block in $k^{th}$ frame, then, $$s_k^i = \frac{\sum_{(x,y) \in B_k^i} F_k^g(x, y)}{\text{Size}(B_k^i)} \to (2)$$

wherein $F_k^g$ contains the green channel intensities of the $k^{th}$ frame and Size (•) provides the size. Typically heart beat from a range of 42 to 240 beat-per-minute (bpm) thus band-pass filter for the frequency ranging from 0.7 to 4 Hz is applied to filter the noise. Furthermore, in an embodiment, the non-stationary trends in the signals may be reduced using Detrending filter.

Figure 2:
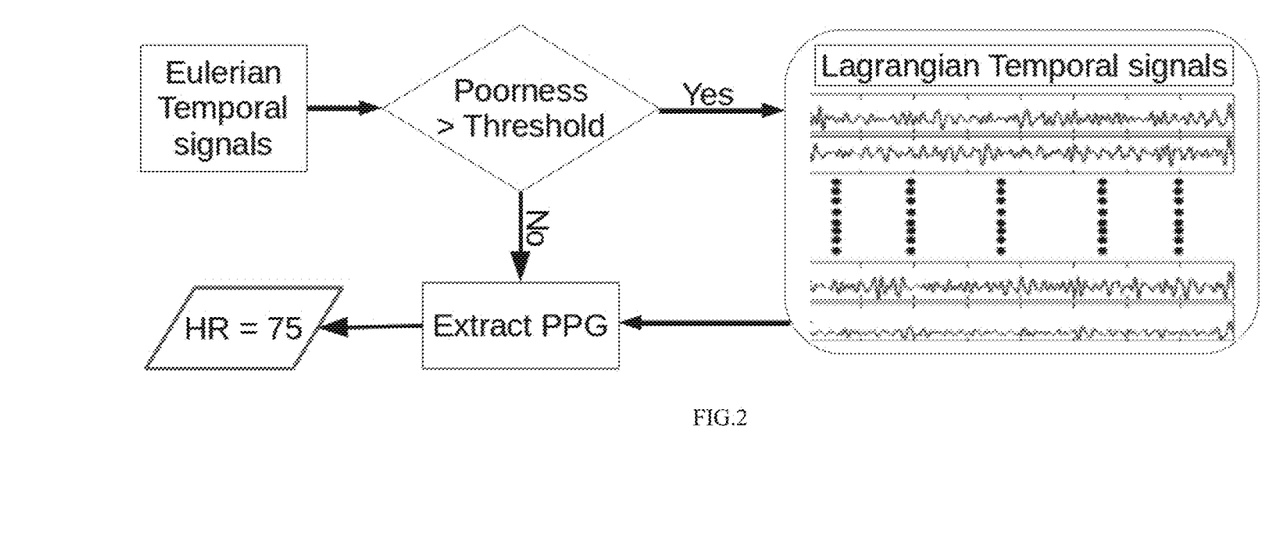
FIG. 2 illustrates an exemplary high-level flow chart illustrating a computer implemented method for serial fusion of Eulerian and Lagrangian approaches for real-time heart rate estimation, in accordance with an embodiment of the present disclosure

Serial Fusion: In accordance with the present disclosure, serial fusion is based on the observation that in some cases Eulerian temporal signals fail to provide accurate HR due to improper illumination, inappropriate camera focus or human factors (for example, skin color). A poorness measure is defined to identify such cases, i.e., measure the efficacy of Eulerian temporal signals. If it is large, temporal signals may be extracted using Lagrangian approach to improve the HR estimation. Accordingly, FIG. 2 illustrates an exemplary high-level flow chart of a computer implemented method for serial fusion of Eulerian and Lagrangian approaches for real-time heart rate estimation, in accordance with an embodiment of the present disclosure.

Figure 3:
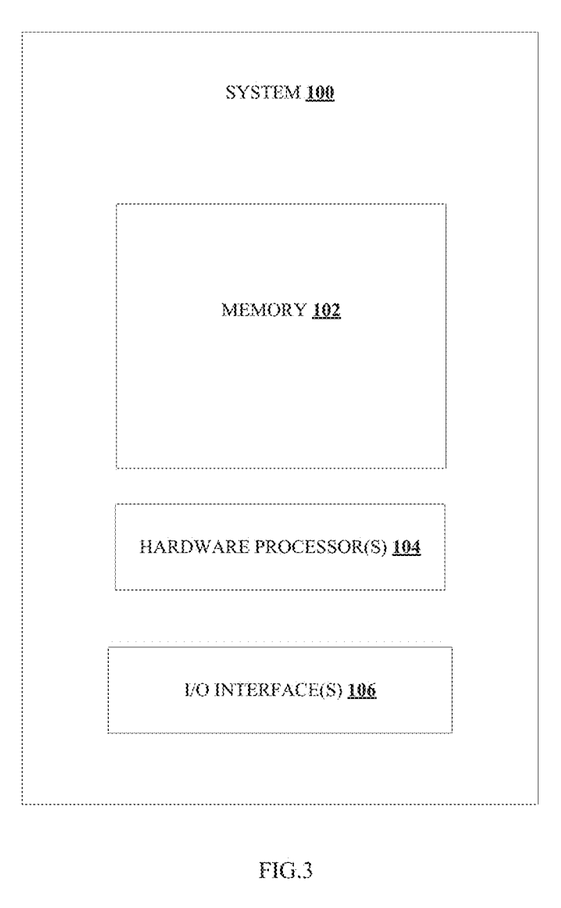
FIG. 3 illustrates an exemplary block diagram of a system for serial fusion of Eulerian and Lagrangian approaches for real-time heart rate estimation, in accordance with an embodiment of the present disclosure.

FIG. 3 illustrates an exemplary block diagram of a system 100 for serial fusion of Eulerian and Lagrangian approaches for real-time heart rate estimation, in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 4:
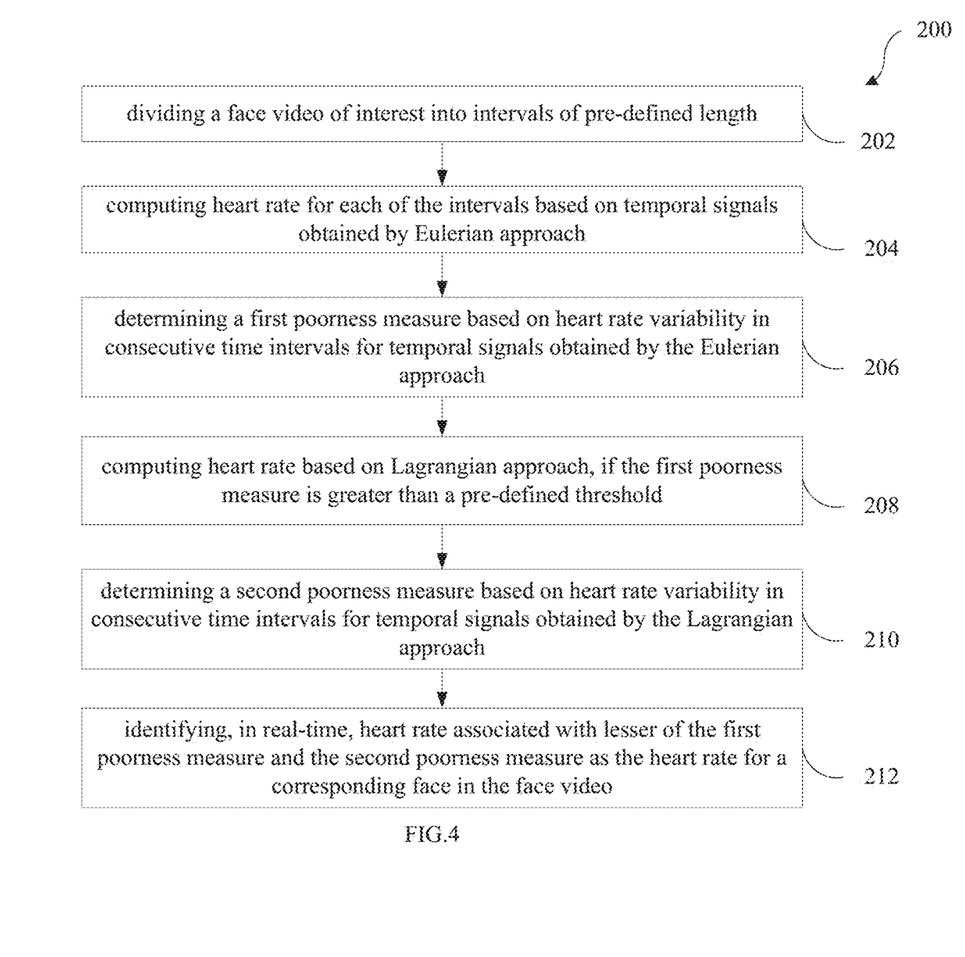
FIG. 4 is an exemplary flow diagram illustrating a computer implemented method for serial fusion of Eulerian and Lagrangian approaches for real-time heart rate estimation, in accordance with an embodiment of the present disclosure.

FIG. 4 is an exemplary flow diagram illustrating a computer implemented method 200 for serial fusion of Eulerian and Lagrangian approaches for real-time heart rate estimation, in accordance with an embodiment of the present disclosure. In an embodiment, the system 100 comprises one or more data storage devices or memory 102 operatively coupled to the one or more processors 104 and is configured to store instructions configured for execution of steps of the method 200 by the one or more processors 104.

Ideally, the HR varies continuously with time, but the variations are small. In accordance with the present disclosure, HR variability in consecutive time intervals is used to define the poorness measure. Accordingly, in accordance with the present disclosure, the one or more processors 104 are configured to divide, at step 202, a face video of interest into intervals of pre-defined length. In an embodiment, the pre-defined length of the intervals is such that the length is not small otherwise peak due to noise can be observed while it should not be large otherwise few HR variability are available. In an embodiment, the pre-defined length is 180 frames. In accordance with the present disclosure, the one or more processors 104 are configured to compute heart rate, at step 204, for each of the intervals based on temporal signals obtained by Eulerian approach. The amplitudes of the temporal signal in an interval vary according to facial structure, thus these are normalized using z-score normalization which keeps the signal shape intact. Mathematically, $i^{th}$ signal of $j^{th}$ interval, T(i,j) is normalized using:

$$T_{(i,j)} \frac{T_{(i,j)} - \text{mean}(T_{(i,j)})}{\text{std}(T_{(i,j)})} \to (3)$$

wherein and mean (•) and std (•) denotes the mean and standard deviation respectively. Moreover, each temporal signal in an interval contains PPG signal corrupted by noise. Thus, $$T_{(i,j)}^t = M P^t + \varepsilon^t \to (4)$$

wherein $p^t$ and $\varepsilon^t$ denote the PPG signal and noise respectively at time instant t while M represents the transformation matrix. The aim is to recover PPG signal in an interval which is given by:

$$O_e^t = Q T_{(i,j)}^t \to (5)$$

wherein $O_e^t$ is the estimated PPG at time t and Q represents an appropriate transformation matrix. Hence it may be seen from equations (4) and (5) that $$O_e^t = ZP^t + \hat{\varepsilon}^t \rightarrow (6)$$

wherein $Z=QM$ and $\hat{\varepsilon}^t = Q\hat{\varepsilon}^t$.

Moreover, it is essential that an accurately estimated PPG be equal to the actual PPG, i.e. $P_e \approx P_a$.

Hence magnitude of Z needs to take the value 1 to avoid scaling and making the shape of estimated and actual PPG similar.

Normally, local PPG is peaked at one frequency that corresponds to HR frequency and it possesses small amplitude at other frequencies. Essentially, it contains high Kurtosis statistics that measures peakedness and tail of a signal. Hence, in accordance with the present disclosure, the following objective function which maximizes the Kurtosis statistics, is used for PPG estimation:

$$\max_Z |\text{Kurtosis}[O_e]| \text{ such that } Z^*Z=1 \rightarrow (7)$$

wherein |•| and Kurtosis [•] represent the absolute value and Kurtosis operators respectively while * denotes a conjugate. The global solution of equation (7) may be attained using methods known in the art.

The HR of an interval is estimated, in accordance with the present disclosure, from $O_e$ using Fast Fourier Transform (FFT) analysis.

The number of samples required in FFT depends on the total number of frames per seconds. It is observed that acquisition of the first frame and saving of the last frame in the face video takes large time as compared to the interframe acquisition time. The number of frames per seconds is affected by these issues, hence it is increased by 0.5 before the FFT analysis. In accordance with the present disclosure, $O_e$ is transformed to frequency domain using FFT and the HR for the $i^{th}$ interval, $h_i$ is given by:

$$h_i = f_t \times 60 \rightarrow (8)$$

wherein $f_t$ is the frequency corresponding to the maximum amplitude in the $i^{th}$ interval.

There may be small variations in heart rate (heart rate variability) in the consecutive time intervals which do not impact the poorness measure and the poorness measure keeps on increasing as the change increases. To leverage this, a first poorness measure is determined, at step 206, for a complete Eulerian temporal signal, $P_m$, in accordance with the present disclosure and is defined as:

$$P_m = \sum_{j=2}^{p} G(|h_j - h_{j-1}|) \rightarrow (9)$$

wherein p and |•| denote the total number of intervals and the absolute value respectively while function G is given by:

$$G(x) = \begin{cases} 0, \text{ if } x < \alpha \\ \frac{(1-e^{(\alpha-x)})}{1+e^{(\alpha-x)}}, \text{ otherwise} \end{cases} \rightarrow (10)$$

wherein the parameter a represents the permissible variations in HR and in an embodiment, it may be set to 5 bpm. It may be noted that domain of function G is non-negative due to the use of absolute value operation in equation (9). If $P_m$ is lower than a pre-defined threshold, th then estimated Eulerian temporal signals are used for HR estimation. In accordance with the present disclosure, the pre-defined threshold th is given by th=p/3 wherein p is the number of intervals. While $P_m$>th indicates HR variations which in turn implies that Eulerian temporal signals are incapable for accurate HR estimation. In such a case, the one or more processors 104 are configured to compute, at step 208, the HR and at step 210, a second poorness measure using the temporal signals derived from the Lagrangian approach. The Lagrangian approach explicitly tracks the distinguishable facial features in the face videos and the variations in the vertical direction are considered to generate the temporal signals. The HR at steps 204 and 208 is estimated by solving equations (7) and (8) while the first poorness measure at step 206 and the second poorness measure at step 210 are defined using equations (9) and (10). In an embodiment of the present disclosure, the one or more processors 104 are configured to identify, at step 212, the HR corresponding to the minimum poorness measure or lesser of the first poorness measure and the second poorness measure as the HR for a corresponding face in the face video. The HR corresponding to each face in the face video is detected similarly when multiple faces are present in the face video.

Experimental Results

Experimental setup: MATLAB 2015a is used to implement the system of the present disclosure on Intel i5-2400 CPU 3.10 GHz. For evaluation, 45 face videos were acquired from 20 subjects using a Logitech webcam C270 camera. The subjects were asked to sit in front of laptop mounted with camera and they were allowed to perform natural facial movements, for example eye blinking, small lip movements and slight tilting of the head. Natural illumination was maintained for acquisition of 40 second long videos at 28 frames per second. The actual PPG was also acquired synchronously by placing CMS 50D+ pulse oximeter on the right index fingertip for ground truth.

Bland-Altman (BA) plot is used to understand the efficacy of the proposed system. It evaluates the consensus among two measurements and clearly distinguish the possible outliers (or systematic error) containing large difference in the measurements. In the paper, two measurements are the actual and predicted HR. For better understanding, consider that a and b represent the ground-truth HR determined from pulse oximeter and the estimated HR respectively. Then abscissas of the BA plot denote the average HR $$\left(viz., \frac{a+b}{2}\right)$$

while the ordinate denotes the error in the HR (i.e., a-b). The good performance is indicated when true value is close to the predicted value, i.e., the ordinate should be close to a straight line given by y=0. More clearly, the parameters mean, variance (denoting fluctuations around the mean) and slope of the error shown in BA plots are close to zero. For more rigorous experimentation, the mean and variance are explicitly shown along with time comparisons and percentages of samples with absolute error less than 5 and 10 bpm. The lower value of these parameters indicates better performance.

Experimental Analysis

Figure 5A:
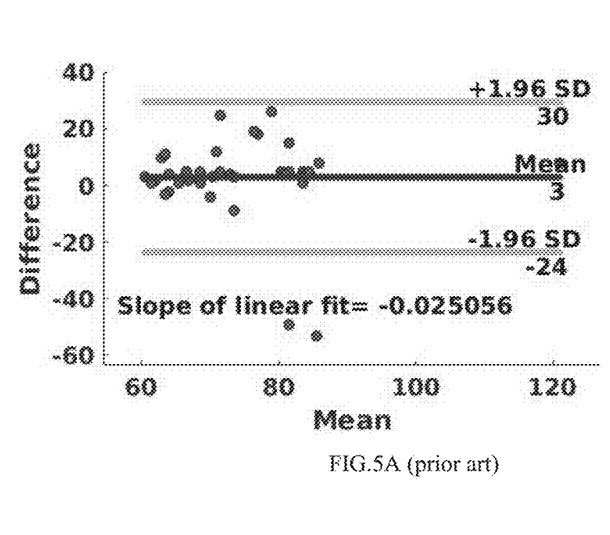
FIG. 5A and FIG. 5B illustrate Bland-Altman (BA) plots for system I and system II respectively, system I and system II being known in the art.
Figure 5B:
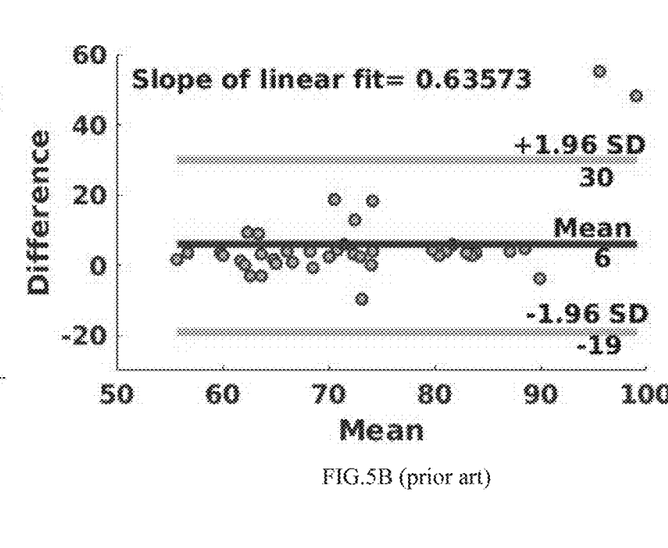
Figure 6A:
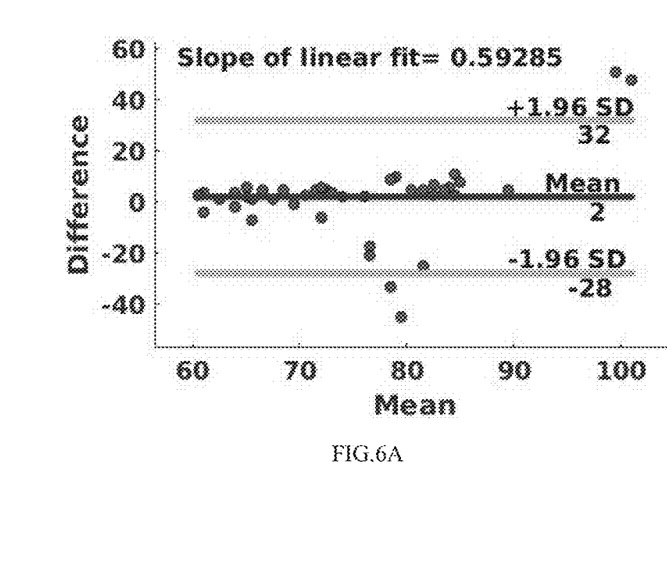
FIG. 6A and FIG. 6B illustrate Bland-Altman (BA) plots for system III and system IV respectively.
Figure 6B:
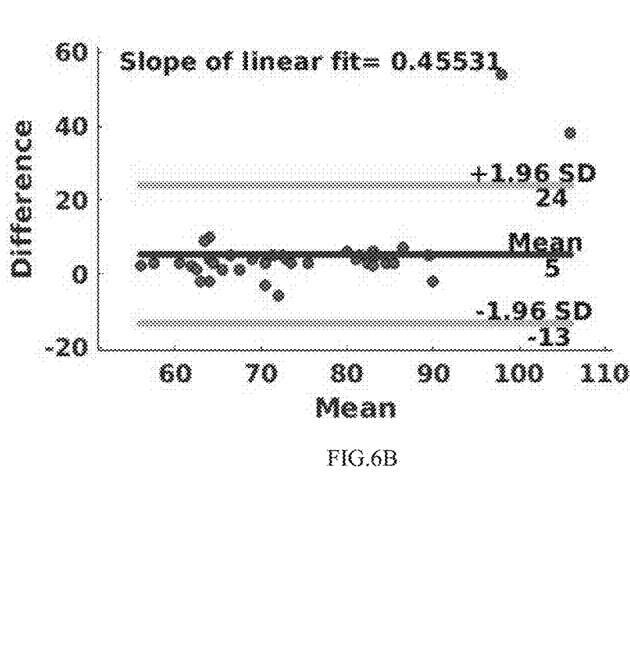
Figure 7A:
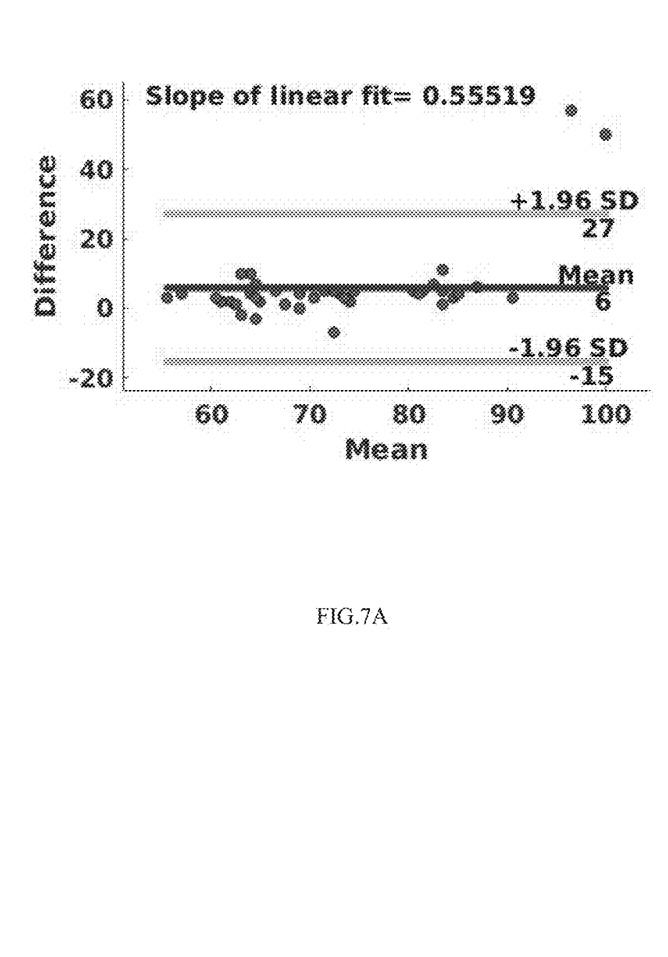
FIG. 7A and FIG. 7B illustrate Bland-Altman (BA) plots for system V and the system in accordance with an embodiment of the present disclosure respectively.
Figure 7B:
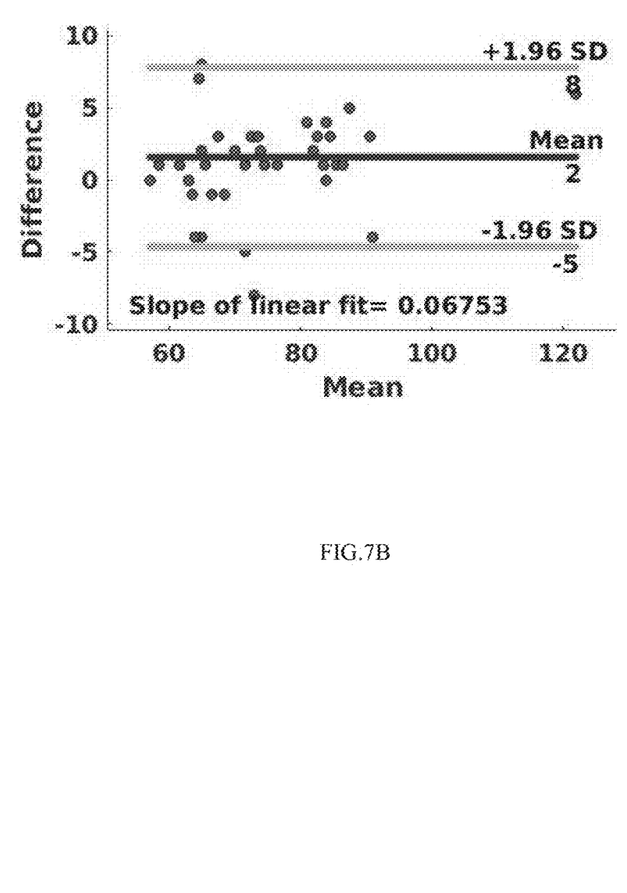

FIGS. 5 through 7 and Table 1 depict the BA plots and performance measures respectively of systems known in the art and the system of the present disclosure.

TABLE 1

Comparative results of HR estimation

| System | Mean* | Variance* | Time (sec)# | Correct$_5$+ | Correct$_{10}$+ |
|---|---|---|---|---|---|
| I | 2.98 | 13.78 | 14.92 | 69% | 80% |
| II | 5.77 | 12.29 | 6.96 | 71% | 88% |
| III | 2.45 | 15.30 | 18.89 | 60% | 82% |
| IV | 5.43 | 9.63 | 5.97 | 78% | 96% |
| V | 6.48 | 10.72 | 20.36 | 78% | 93% |
| Present disclosure | 1.80 | 3.06 | 6.43 | 87% | 100% | wherein system I is the system disclosed in "*Detecting pulse from head motions in video*" by G. Balakrishnan et al. in *IEEE Conference on Computer Vision and Pattern Recognition* wherein the Lagrangian approach followed by Principal Component Analysis and FFT are used;

system II is the system disclosed in "*Advancements in non-contact, multiparameter physiological measurements using a webcam*" by Ming-Zher Poh et al. in *IEEE Transactions on Biomedical Engineering* wherein three temporal signals are extracted using each color channel followed by independent Component Analysis and FFT to estimate HR;

system III replaces serial fusion of the present disclosure by parallel fusion, i.e. it does not require the poorness measure and instead employs both the Eulerian and Lagrangian temporal signals for all the face videos;

system IV estimates the HR using only Eulerian temporal signals and avoids Lagrangian temporal signals and poorness measure;

system V evaluates two HRs and poorness measure using Eulerian and Lagrangian temporal signals, but the HR corresponding to the lower poorness measure is marked as the final estimated HR;

+: Correct$_5$ and Correct$_{10}$ denote percentage of samples with absolute error less than 5 and 10 bpm respectively;

*: Mean and Variance of the error shown in BA plots viz., FIGS. 5 through 7; and

: Time required in seconds for the face videos of 40 seconds.

Particularly, FIG. 5A and FIG. 5B illustrate Bland-Altman (BA) plots for system I and system II respectively, system I and system II being known in the art; FIG. 6A and FIG. 6B illustrate Bland-Altman (BA) plots for system III and system IV respectively; and FIG. 7A and FIG. 7B illustrate Bland-Altman (BA) plots for system V and the system in accordance with an embodiment of the present disclosure respectively. It may be noted from the FIGS. 5 through 7 and Table 1 herein above that:

1) The lowest performance is depicted by system I. It is mainly due to the time expensive and inaccurate facial feature tracking. Likewise, system II depicts poor performance because it considers a complete face region as ROI. Moreover, systems I and II employ different PPG extraction that result in spurious HR estimation.

2) Fusion does not always guarantee the performance improvement and instead performance can be degraded if inappropriate features are fused. Similar behavior can be observed by comparing system III and system IV. Even though system III employs both Lagrangian and Eulerian temporal signals, its performance is lower than system IV which require only Eulerian temporal signal. The peculiar behavior is because Lagrangian temporal signals are erroneous in some cases and in those cases, better HR can be obtained using only Eulerian temporal signals but use of both Eulerian and Lagrangian temporal signals has degraded the performance. A better fusion strategy is designed in system V where HR is selected according to the poorness measure of Eulerian and Lagrangian temporal signals. It fails to perform accurately when Lagrangian temporal signals saturate after some time due to tracking error which further results in low HR variability and spurious HR estimation. When the system of the present disclosure is used, evaluation of Lagrangian temporal signals is avoided in most of these cases due to the serial fusion. Hence, the system of the present disclosure performs better than System IV in terms of minimizing the errors (Correct$_5$ and Correct$_{10}$), mean and variance.

3) Systems III and V are computationally expensive because they use Eulerian and Lagrangian temporal signals in all the cases. Lower time computation is observed in the system of the present disclosure because it sometimes avoids time consuming Lagrangian temporal signal due to the serial fusion. The least computational time is shown by System IV because it completely avoids the Lagrangian temporal signals. The time difference between the system of the present disclosure and System IV is 0.54 seconds that can be considered insignificant for the face videos of duration of 40 seconds. Keeping in view the performance improvement, the system of the present disclosure advocates the serial fusion.

4) The system of the present disclosure can estimate the HR in 6.43 seconds for the 40 seconds long face video. It points out that the system of the present disclosure can be employed in near real-time situations.

Thus in accordance with the present disclosure, systems and methods described herein above estimate accurate and near real-time HR by employing face videos consisting of frontal, profile and multiple faces acquired in a non-contact manner. The artifacts introduced due to facial expressions, respiration, eye blinking and environmental factors have been mitigated. Despite this, the Eulerian temporal signals have failed to provide accurate HR in some cases. Such cases have been identified by defining a poorness measure and both the Eulerian and Lagrangian temporal signals are employed in these cases for better HR estimation. Experimental results have demonstrated the superiority of the system of the present disclosure over existing well known systems. Moreover, it has shown that better performance is expected when the serial fusion as described in the present disclosure is used instead of parallel fusion.

The written description describes the subject matter herein to enable any person skilled in the art to make and use the embodiments of the present disclosure. The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

The scope of the subject matter embodiments defined here may include other modifications that occur to those skilled in the art. Such other modifications are intended to be within the scope if they have similar elements that do not differ from the literal language of the claims or if they include equivalent elements with insubstantial differences from the literal language.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments of the present disclosure may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules comprising the system of the present disclosure and described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device. The various modules described herein may be implemented as software and/or hardware modules and may be stored in any type of non-transitory computer readable medium or other storage device. Some non-limiting examples of non-transitory computer-readable media include CDs, DVDs, BLU-RAY, flash memory, and hard disk drives.

Further, although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

What is claimed is:

1. A processor implemented method (200) comprising:
    dividing a face video of interest into intervals of pre-defined length (202);
    computing heart rate (HR) for each of the intervals based on temporal signals obtained by Eulerian approach (204);
    determining a first poorness measure based on heart rate variability in consecutive time intervals for temporal signals obtained by the Eulerian approach (206);
    computing heart rate based on Lagrangian approach, if the first poorness measure is greater than a pre-defined threshold (208);
    determining a second poorness measure based on heart rate variability in consecutive time intervals for temporal signals obtained by the Lagrangian approach (210); and
    identifying, in real-time, heart rate associated with lesser of the first poorness measure and the second poorness measure as the heart rate for a corresponding face in the face video (212).

2. The processor implemented method of claim 1, wherein the pre-defined length is 180 frames.

3. The processor implemented method of claim 1, wherein the pre-defined length is optimized such that peak due to noise is averted and HR variability is available.

4. The processor implemented method of claim 1, wherein the step of determining the first poorness measure and the step of determining the second poorness measure comprises:
    normalizing the temporal signals in an interval;
    maximizing Kurtosis associated with the normalized temporal signal to extract photoplethysmogram (PPG) signal;
    transforming the PPG signal to frequency domain;
    computing the heart rate based on frequency corresponding to maximum amplitude associated with the PPG signal; and
    computing the first poorness measure or the second poorness measure as a function of the heart rate variability in consecutive time intervals and permissible variations in heart rate in beats per minute (bpm).

5. The processor implemented method of claim 1, wherein the pre-defined threshold is based on number of intervals.

6. The processor implemented method of claim 5, wherein the pre-defined threshold is one third of the number of intervals.

7. A system (100) comprising:
    one or more data storage devices (102) operatively coupled to one or more hardware processors (104) and configured to store instructions configured for execution by the one or more hardware processors to:
    divide a face video of interest into intervals of pre-defined length;
    compute heart rate (HR) for each of the intervals based on temporal signals obtained by Eulerian approach;
    determine a first poorness measure based on heart rate variability in consecutive time intervals for temporal signals obtained by the Eulerian approach;
    compute heart rate based on Lagrangian approach, if the first poorness measure is greater than a pre-defined threshold;

determine a second poorness measure based on heart rate variability in consecutive time intervals for temporal signals obtained by the Lagrangian approach; and identify, in real-time, heart rate associated with lesser of the first poorness measure and the second poorness measure as the heart rate for a corresponding face in the face video.

8. The system of claim 7, wherein the pre-defined length is 180 frames.

9. The system of claim 7, wherein the pre-defined length is optimized such that peak due to noise is averted and HR variability is available.

10. The system of claim 7, wherein the one or more hardware processors are further configured to determine the first poorness measure and the second poorness measure by:
normalizing the temporal signals in an interval;
maximizing Kurtosis associated with the normalized temporal signal to extract photoplethysmogram (PPG) signal;
transforming the PPG signal to frequency domain;
computing the heart rate based on frequency corresponding to maximum amplitude associated with the PPG signal; and
computing the first poorness measure or the second poorness measure as a function of the heart rate variability in consecutive time intervals and permissible variations in heart rate in beats per minute (bpm).

11. The system of claim 7, wherein the pre-defined threshold is based on number of intervals.

12. The system of claim 11, wherein the pre-defined threshold is one third of the number of intervals.

13. A computer program product comprising a non-transitory computer readable medium having a computer readable program embodied therein, wherein the computer readable program, when executed on a computing device, causes the computing device to:
divide a face video of interest into intervals of pre-defined length;
compute heart rate (HR) for each of the intervals based on temporal signals obtained by Eulerian approach;
determine a first poorness measure based on heart rate variability in consecutive time intervals for temporal signals obtained by the Eulerian approach;
compute heart rate based on Lagrangian approach, if the first poorness measure is greater than a pre-defined threshold;
determine a second poorness measure based on heart rate variability in consecutive time intervals for temporal signals obtained by the Lagrangian approach; and
identify, in real-time, heart rate associated with lesser of the first poorness measure and the second poorness measure as the heart rate for a corresponding face in the face video.

* * * * *